United States Patent [19]

Jansen et al.

[11] Patent Number: 5,621,152

[45] Date of Patent: Apr. 15, 1997

[54] PROCESS FOR REMOVING OLEFINIC IMPURITIES FROM 2H-HEPTAFLUOROPROPANE (R 227)

[75] Inventors: Rolf-Michael Jansen, Kelkheim; Peter Hopp, Hofheim, both of Germany

[73] Assignee: Hoechst Aktiengesellschaft, Germany

[21] Appl. No.: 616,483

[22] Filed: Mar. 19, 1996

[30] Foreign Application Priority Data

Mar. 21, 1995 [DE] Germany .................. 195 10 159.6

[51] Int. Cl.⁶ .................. C07C 17/38; C07C 17/389; C07C 19/08
[52] U.S. Cl. .................................................. 570/179
[58] Field of Search .................................. 570/179

[56] References Cited

U.S. PATENT DOCUMENTS

| | | |
|---|---|---|
| 2,909,570 | 10/1959 | Wade et al. .................. 570/179 |
| 3,026,359 | 3/1962 | Mastrangelo et al. . |
| 3,696,156 | 10/1972 | Weeks . |
| 5,300,714 | 4/1994 | Pothapragada et al. . |

FOREIGN PATENT DOCUMENTS

| | | |
|---|---|---|
| 2068128 | 11/1992 | Canada . |
| 0457613 | 11/1991 | European Pat. Off. . |
| 0512502 | 11/1992 | European Pat. Off. . |

*Primary Examiner*—Joseph E. Evans
*Attorney, Agent, or Firm*—Connolly and Hutz

[57] ABSTRACT

Process for removing olefinic impurities from 2H-heptafluoropropane (R 227).

The invention relates to a process for removing olefinic impurities from 2H-heptafluoropropane (R 227) by passing the contaminated R 227 in the gas phase at from −20° to 100° C. over aluminum oxide.

5 Claims, No Drawings

PROCESS FOR REMOVING OLEFINIC IMPURITIES FROM 2H-HEPTAFLUOROPROPANE (R 227)

DESCRIPTION

Process for removing olefinic impurities from 2H-heptafluoropropane (R 227).

The chlorine-free, only partially fluorinated hydrocarbon (H-FC) 2H-heptafluoropropane (R 227) is a very suitable substitute for the CFCs used hitherto as propellant in pharmaceutical aerosols. However, in the preparation of R 227 from hexafluoropropene (HFP), the formation of toxic olefinic by-products cannot be completely prevented. Likewise, the presence of traces of the olefinic starting material HFP in the R 227 cannot be avoided. For use of R 227 as pharmaceutical aerosols, these olefinic impurities have to be completely removed, even if they are only present in the ppm range.

It is known that olefinic impurities can be removed from R 227 using, for example, alcohols and a base (EP-A-0 512 502). However, this presents the problem of subsequently again having to remove the unreacted residues of the alcohol completely from the R 227. Furthermore, the fluorinated ethers formed in this reaction have to be eliminated at some expense.

U.S. Pat No. 3,696,156 discloses the removal of perfluoroolefins or perfluorochloroolefins from saturated perhalogenated fluorocarbons having from 2 to 6 carbon atoms in the gas phase at relatively high temperatures of from 180° to 250° C. In this method, the gaseous starting material is passed over aluminum oxide containing a basic compound such as an alkali metal hydroxide or oxide. The temperatures should not be below those specified (column 4, lines 12 to 19). The presence of the basic compounds on the aluminum oxide is likewise necessary (column 3, lines 52 to 66).

According to EP-A-0 457 613, the liquid higher homologs of said perhalogenated compounds can be purified in a similar manner at a temperature as low as room temperature, for example liquid perfluoroalkanes having from 5 to 8 carbon atoms. In this method, preference is again given to using aluminum oxide which has been coated with alkali metal or alkaline earth metal hydroxide or oxide (page 3, lines 9 to 21).

It has now surprisingly been found that olefinic impurities, in particular hexafluoropropene (HFP), can be completely removed from R 227 in the gas phase at temperatures as low as from −20° to 100° C. when the contaminated R 227 is passed over aluminum oxide.

The invention thus provides a process for removing olefinic impurities from 2H-heptafluoropropane (R 227), which comprises passing the contaminated R 227 in the gas phase at from −20° to 100° C. over aluminum oxide. The aluminum oxide preferably contains from 2 to 10% by weight of adsorbed water, in particular from 2 to 8% by weight.

The process is preferably carried out at a temperature of from −20° to 50° C., in particular from 0° to 30°C. The pressure is preferably from 1 to 10 bar.

Preference is given to using γ-aluminum oxide.

Unlike the processes described in U.S. Pat. No. 3,696,156 and EP-A-0 457 613, the aluminum oxide does not have to contain any basic compounds such as alkali metal oxides or hydroxides, or alkaline earth metal oxides or hydroxides. The aluminum oxide is preferably free of such compounds, since these are superfluous in the present process, although they do no harm.

The invention is illustrated by the following example.

EXAMPLE 400 kg of R 227 containing 50 ppm of hexafluoropropene were circulated from a reservoir at a pressure of 5 bar by means of a pump (throughput 50 kg/h) at 25° C. from below through a tube (length=100 cm, diameter=10 cm) packed with 10 kg of aluminum oxide (water content 6% by weight) and then back into the reservoir. After the R 227 had been circulated over the aluminum oxide for 24 hours, the hexafluoropropene content in the R 227 was below the detection limit of 1 ppm.

We claim:
1. A process for removing olefinic impurities from 2H-heptafluoropropane (R 227), which comprises passing the contaminated R 227 in the gas phase at from −20° to 100° C. over aluminum oxide.
2. The process as claimed in claim 1, carried out at a temperature of from −20° to 50° C.
3. The process as claimed in claim 1, carried out at a pressure of from 1 to 10 bar.
4. The process as claimed in claim 1 wherein the aluminum oxide used is in the γ-modification.
5. The process as claimed in claim 1, wherein the aluminum oxide contains from 2 to 10% by weight of adsorbed water.

* * * * *